US011157730B2

United States Patent
Sahoo et al.

(10) Patent No.: US 11,157,730 B2
(45) Date of Patent: Oct. 26, 2021

(54) DETERMINING EXPERIMENTS REPRESENTED BY IMAGES IN DOCUMENTS

(71) Applicant: Scinapsis Analytics Inc., Toronto (CA)

(72) Inventors: Anshuman Sahoo, Toronto (CA); Thomas Kai Him Leung, Toronto (CA); David Qixiang Chen, Toronto (CA); Elvis Mboumien Wianda, Toronto (CA)

(73) Assignee: Scinapsis Analytics Inc., Toronto (CA)

( * ) Notice: Subject to any disclaimer, the term of this patent is extended or adjusted under 35 U.S.C. 154(b) by 0 days.

(21) Appl. No.: 16/450,490

(22) Filed: Jun. 24, 2019

(65) Prior Publication Data

US 2020/0401799 A1     Dec. 24, 2020

(51) Int. Cl.
G06K 9/62       (2006.01)
G06K 9/00       (2006.01)
G06N 20/00      (2019.01)

(52) U.S. Cl.
CPC ..... *G06K 9/00456* (2013.01); *G06K 9/00463* (2013.01); *G06K 9/6256* (2013.01); *G06N 20/00* (2019.01)

(58) Field of Classification Search
CPC .......... G06K 9/00456; G06K 9/00463; G06K 9/6256; G06N 20/00
USPC ...................................................... 382/181
See application file for complete search history.

(56) References Cited

U.S. PATENT DOCUMENTS

| 5,335,290 | A | 8/1994 | Cullen et al. |
| 2011/0252315 | A1 | 10/2011 | Misawa et al. |
| 2014/0358973 | A1* | 12/2014 | Roman ............. G06K 9/00469 707/794 |
| 2015/0170648 | A1* | 6/2015 | King ...................... G06F 3/167 704/235 |
| 2018/0107792 | A1* | 4/2018 | Rajan .................... G16H 10/60 |
| 2018/0189269 | A1* | 7/2018 | Quirk ................... G06F 40/289 |
| 2019/0073444 | A1* | 3/2019 | Berthoumieux ....... G16B 15/00 |
| 2020/0005225 | A1* | 1/2020 | Chaubard ........... G06K 9/3241 |

FOREIGN PATENT DOCUMENTS

| EP | 3702963 A2 | 9/2020 |
| WO | 2018229490 A1 | 12/2018 |

OTHER PUBLICATIONS

Extended European Search Report in corresponding European Patent application No. 20177879.2 dated Nov. 30, 2020 (9 pages).
Ramel, J.Y. et al., "AGORA: The Interactive Document Image Analysis Tool of the BVH Project", Proc. IEEE Computer Society Second International Conference on Document Digital Analysis for Libraries (DIAL '06) Apr. 2006, pp. 145-155 (11pages).

(Continued)

*Primary Examiner* — Stephen P Coleman
(74) *Attorney, Agent, or Firm* — Ferguson Braswell Fraser Kubasta PC

(57) ABSTRACT

A method may include acquiring one or more image texts from an image of a document, segmenting the image into one or more sub-images using the one or more image texts, determining, by applying a machine learning model, one or more experimental techniques of one or more experiments for the one or more sub-images, and adding, to a knowledge base, one or more mappings of the one or more sub-images to the one or more experiments.

17 Claims, 17 Drawing Sheets

(56) References Cited

OTHER PUBLICATIONS

Written Opinion and International Search Report of the International Searching Authority in corresponding international application No. PCT/CA2020/050876 dated Aug. 13, 2020 (8 pages).
Alom, Md Zahangir, "Improved Deep Convolutional Neural Networks (DCCN) Approaches for Computer Vision and Bio-Medical Imaging", Dissertation Submitted to The School of Engineering, University of Dayton, Ohio, Dec 2018; (413 pages).

* cited by examiner

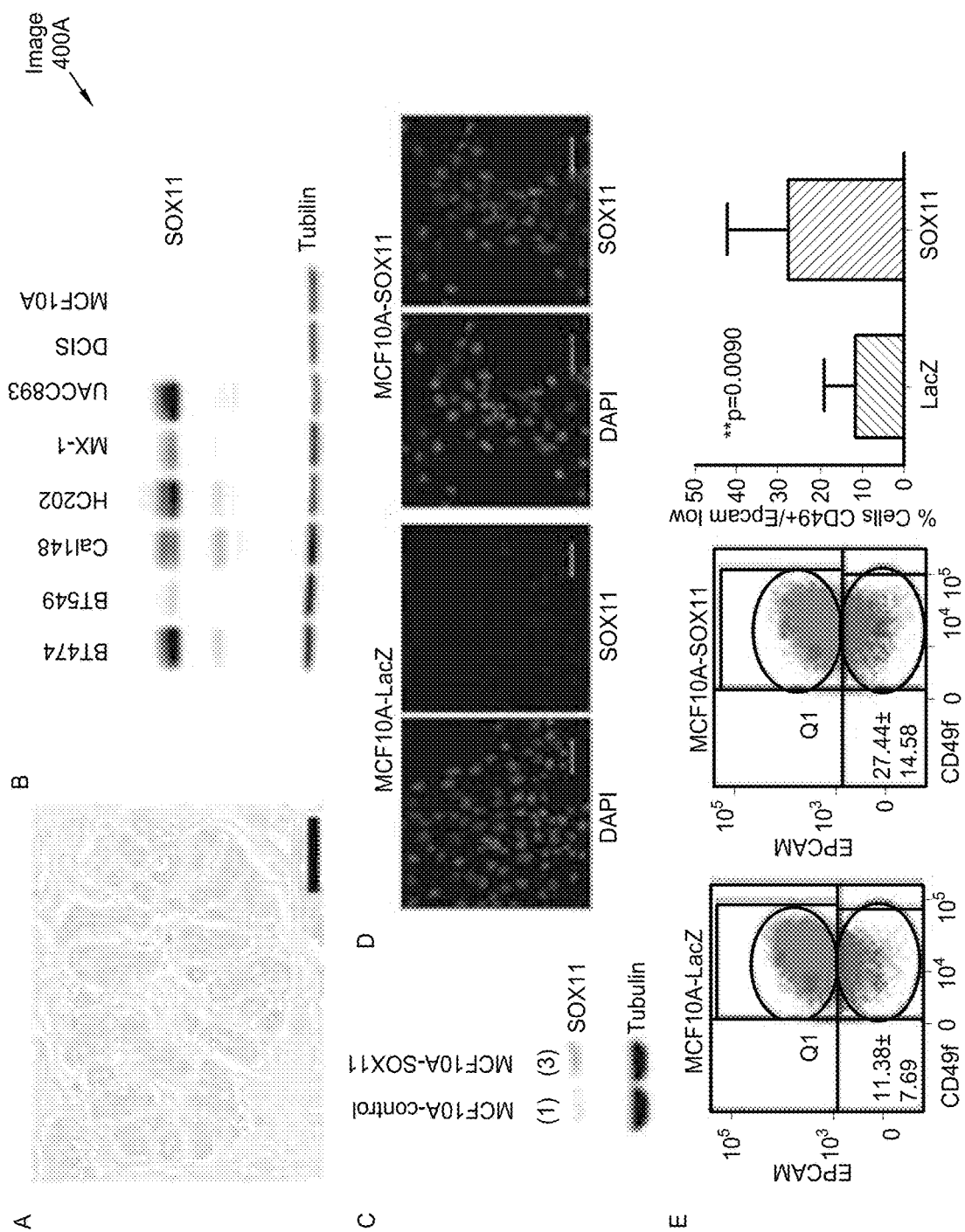
FIG. 4A1

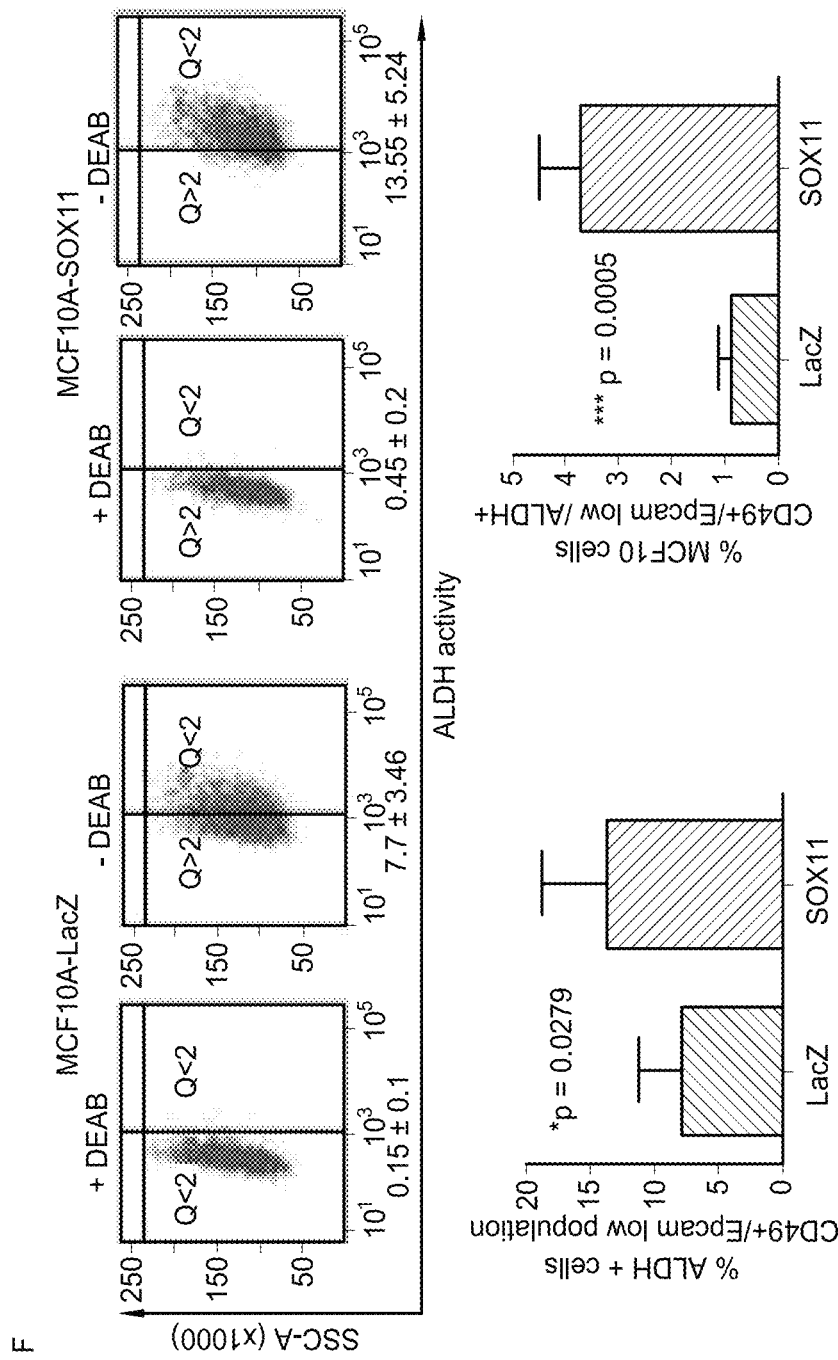
FIG. 4A2

Expression of SOX11 in postnatal mammary epithelial cells alters progenitor cell populations. (A) SOX11 expression was not detected in normal mature breast tissue. Scale bar: 200 μm. (B) SOX11 was expressed in some basal-like breast cancer and HER2+ cell lines, but not in MCF10A or DCIS.com cells (C) Western blot of MCF10A-LacZ control and MCF10A-SOX11 cells. SOX11 levels (indicated by numerical values) were measured by densitometry, and normalized by dividing by the tubulin values. (D) Immunofluorescence staining of MCF10A-LacZ control and MCF10A-SOX11 cells with DAPI (blue in inset) and SOX11 (white). Scale bar: 50 μm. (E) Representative FACS analysis of EpCAM/CD49f-sorted MCF10A control and MCF10A-SOX11 cell populations. Experiments were performed five times. The average percentage of EpCAM--/CD49f+ cells in each population is shown [median ± standard deviation (SD)]. Student's t-test was performed. (F) ALDH activity levels in MCF10A-control and MCF10A-SOX11 cells were detected with the Aldefluor assay. Cells were stained and sorted with CD49f and EpCAM antibodies, and ALDH activity was measured with the Alderfluor kit. Representative ALDH activities after FACS analysis in EpCAM--/CD49f + MCF10A-control and MCF10A-SOX11 cell populations are shown. +DEAB plots display the negative control; cells incubated with diethylaminobenzaldehyde (DEAB), the specific inhibitor of ALDH, were used to establish the baseline fluorescence of these cells. Experiments were performed four times, and Student's t-test was performed. The frequency of EpCAM--/CD49f + basal-like ALDH+ cells (left graph) and EpCAM--/CD49f+ALDH+ cells (right graph) in MCF10A-SOX11 as compared with MCF10-LacZ control populations are shown. Error bars represent SD.

FIG. 4B

Legend Text 410

Sub-Legend Text A 422A — 'A' : [(A) SOX11 expression was not detected in normal mature breast tissue'.' Scale bar: 200 μm]

Sub-Legend Text B 422B — 'B' : [' (B) SOX11 was expressed in some basal-like breast cancer and HER2+ cell lines, but not in MCF10A or DCIS.com cells']

Sub-Legend Text C 422C — 'C' : [' (C) Western blot of MCF10A-LacZ control and MCF10A-SOX11 cells'.' SOX11 levels (indicated by numerical values) were measured by densitometry, and normalized by dividing by the tubulin values']

Sub-Legend Text D 422D — 'D' : [' (D) Immunofluorescence staining of MCF10A-LacZ control and MCF10A-SOX11 cells with DAPI (blue in inset) and SOX11 (white). Scale bar: 50 μm]

Sub-Legend Text E 422E — 'E' : [' (E) Representative FACS analysis of EpCAM/CD49f-sorted MCF10A control and MCF10A-SOX11 cell populations'.' Experiments were performed five times'.' The average percentage of EpCAM–/CD49f+ cells in each population is shown [median ± standard deviation (SD)]. Student's t-test was performed']

Sub-Legend Text F 422F — 'F' : [' (F) ALDH activity levels in MCF10A-control and MCF10A-SOX11 cells were detected with the Aldefluor assay'.' Cells were stained and sorted with CD49f and EpCAM antibodies, and ALDH activity was measured with the Aldefluor kit'.' Representative ALDH activities after FACS analysis in EpCAM–/CD49f + MCF10A-control and MCF10A-SOX11 cell populations are shown'.' +DEAB plots display the negative control; cells incubated with diethylaminobenzaldehyde (DEAB), the specific inhibitor of ALDH, were used to establish the baseline fluorescence of these cells'.' Experiments were performed four times, and Student's t-test was performed'.' The frequency of EpCAM–/CD49f+ALDH+ cells (right graph) in MCF10A-SOX11 as compared with MCF10-LacZ control populations are shown'.' Error bars represent SD']

FIG. 4C

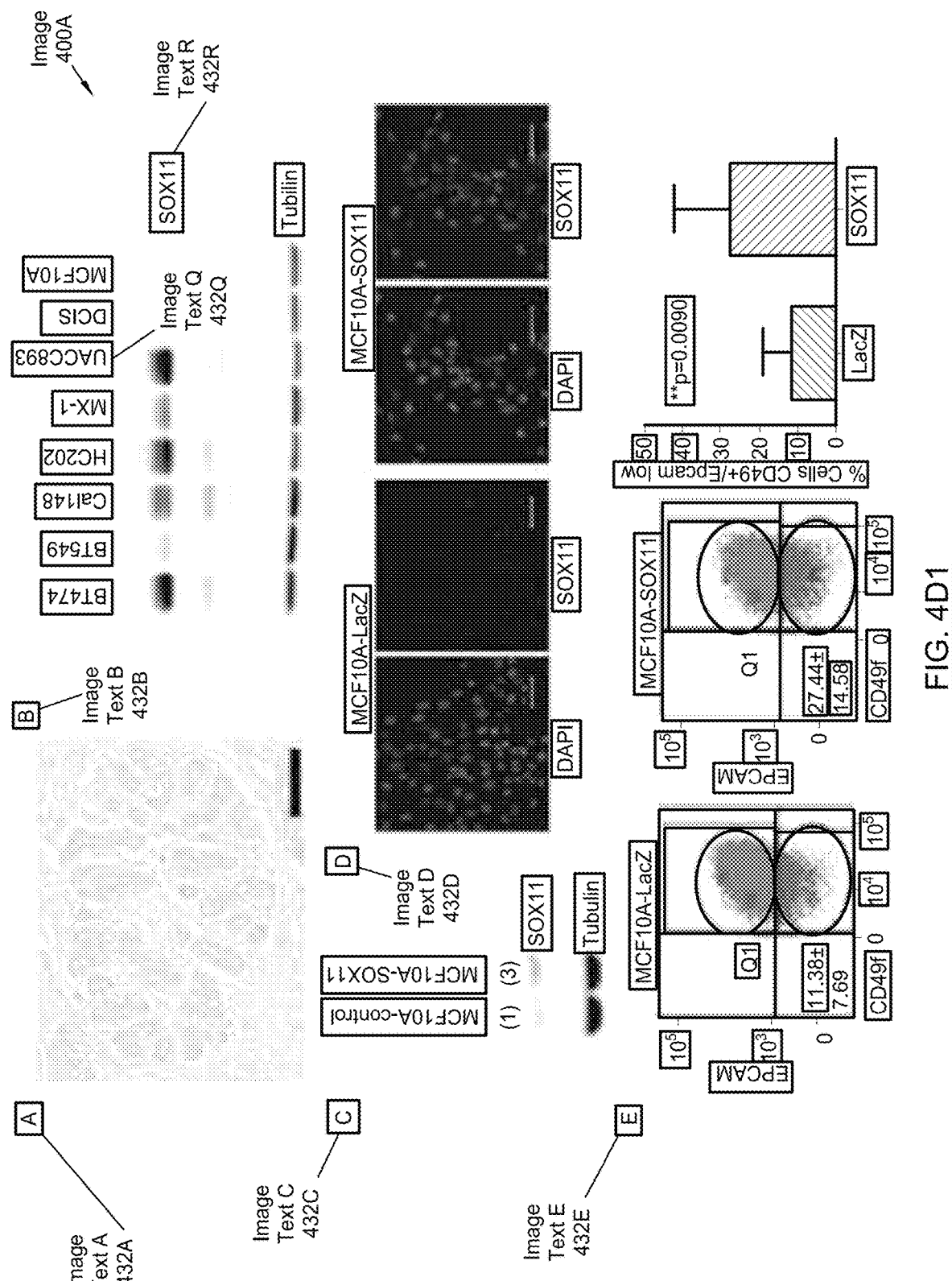
FIG. 4D1

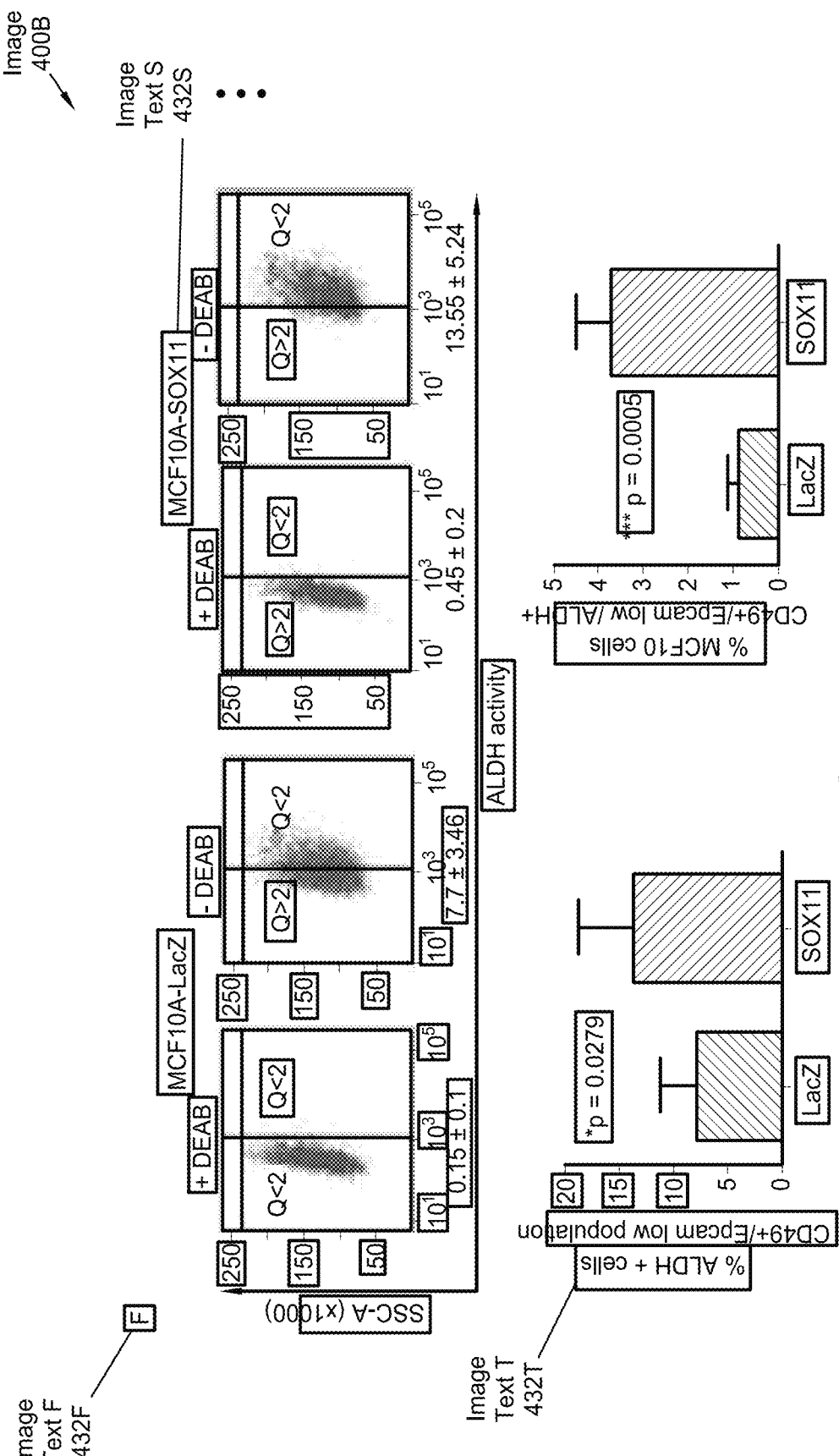
FIG. 4D2

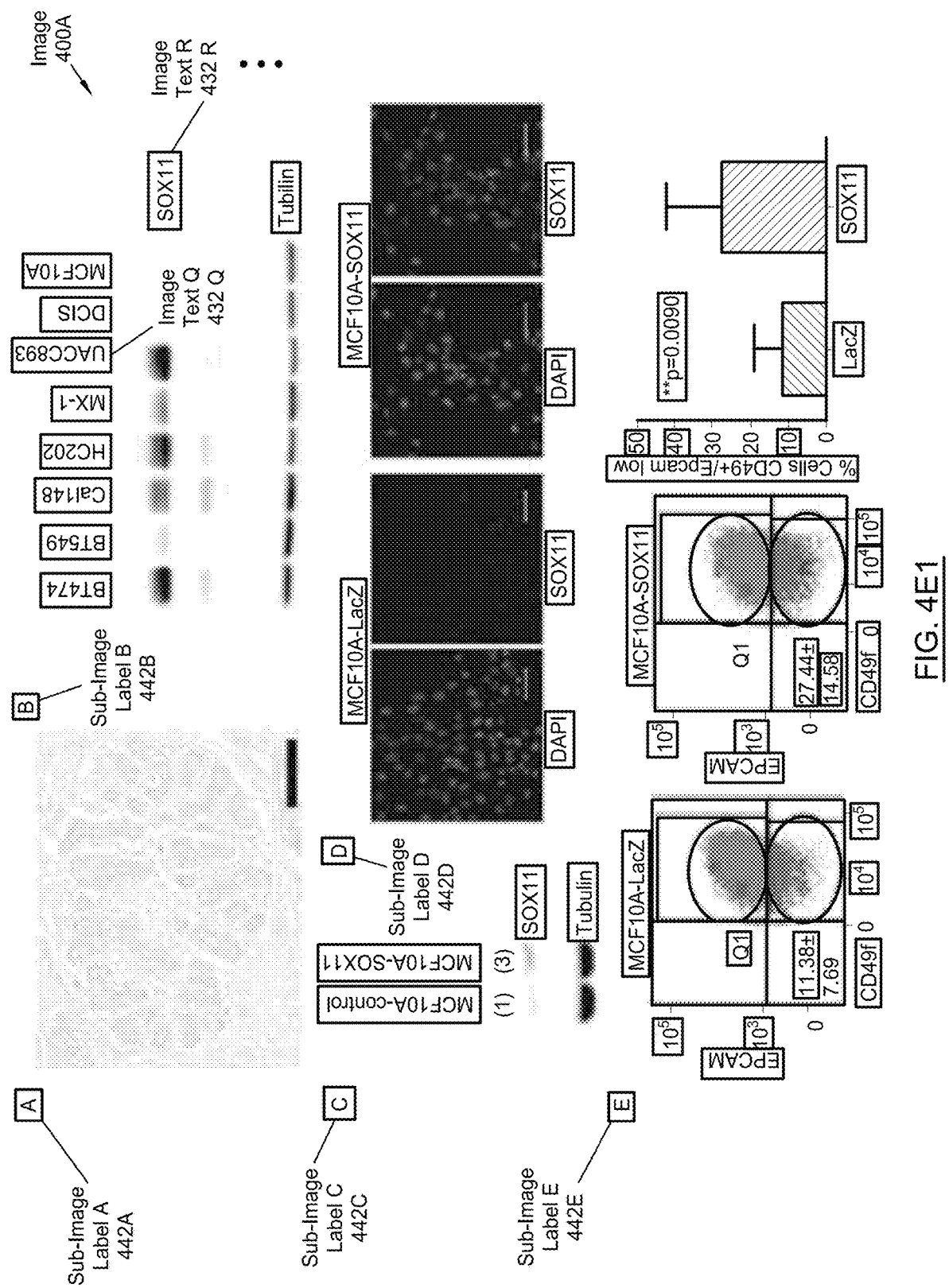
FIG. 4E1

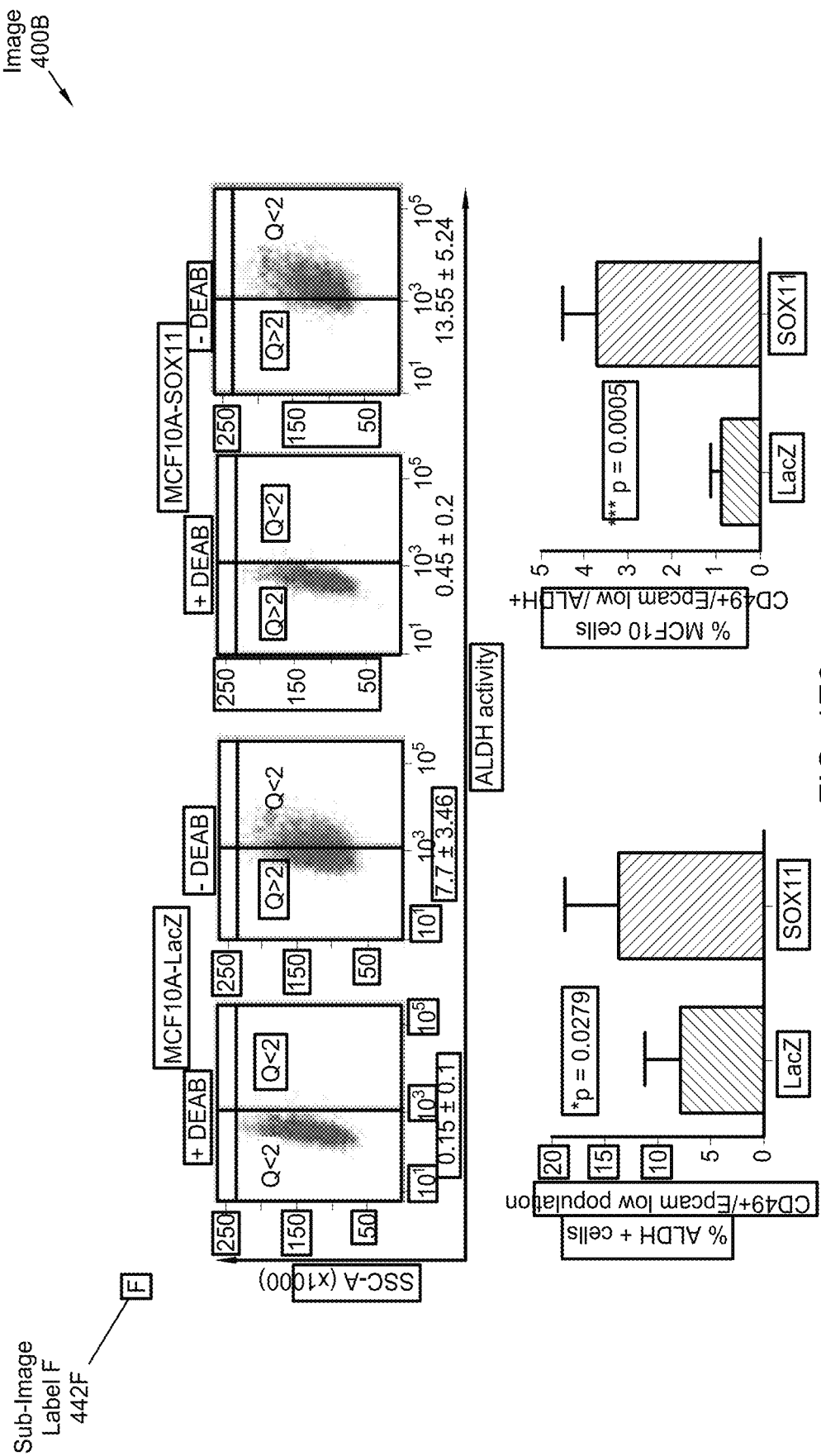
FIG. 4E2

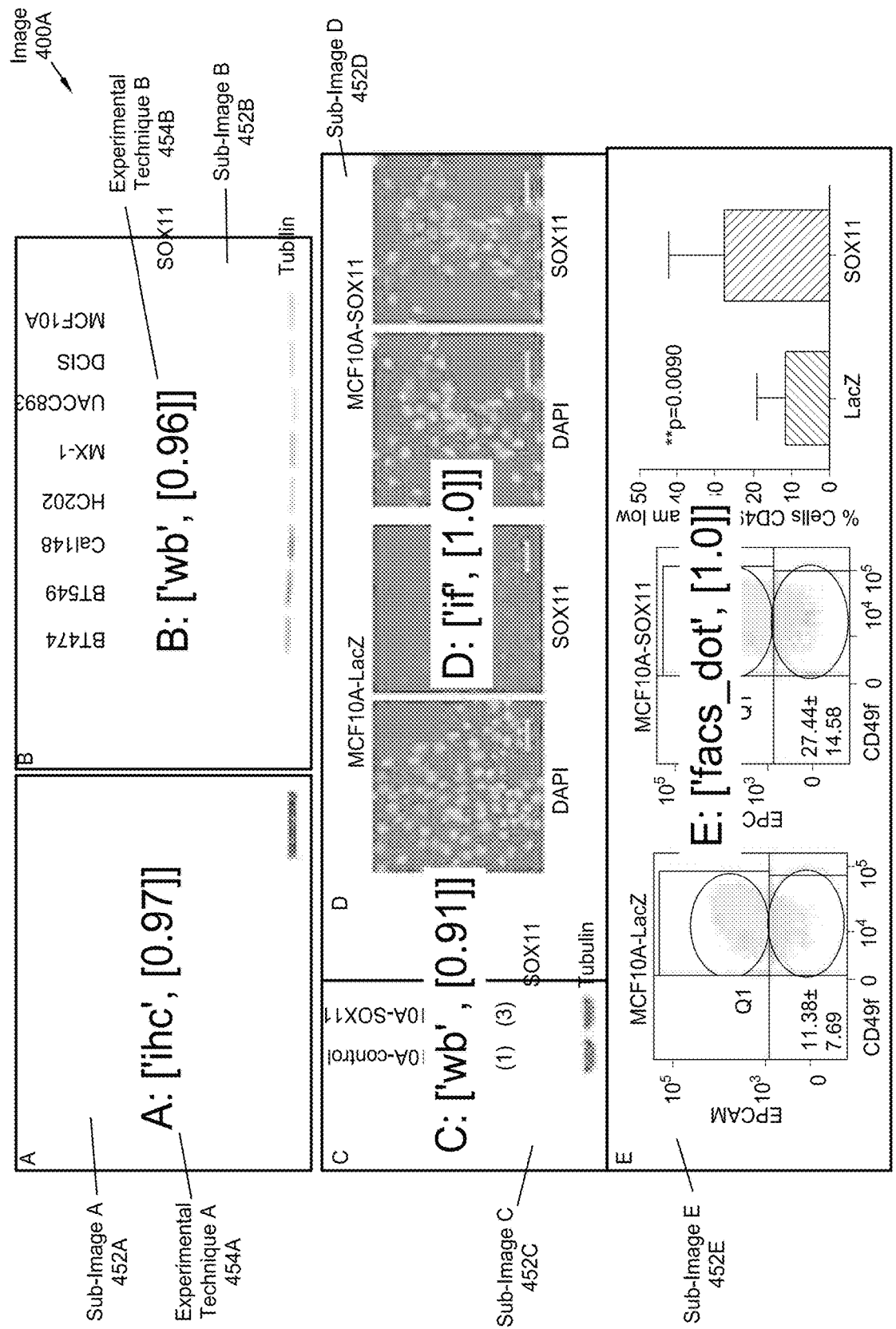
FIG. 4F1

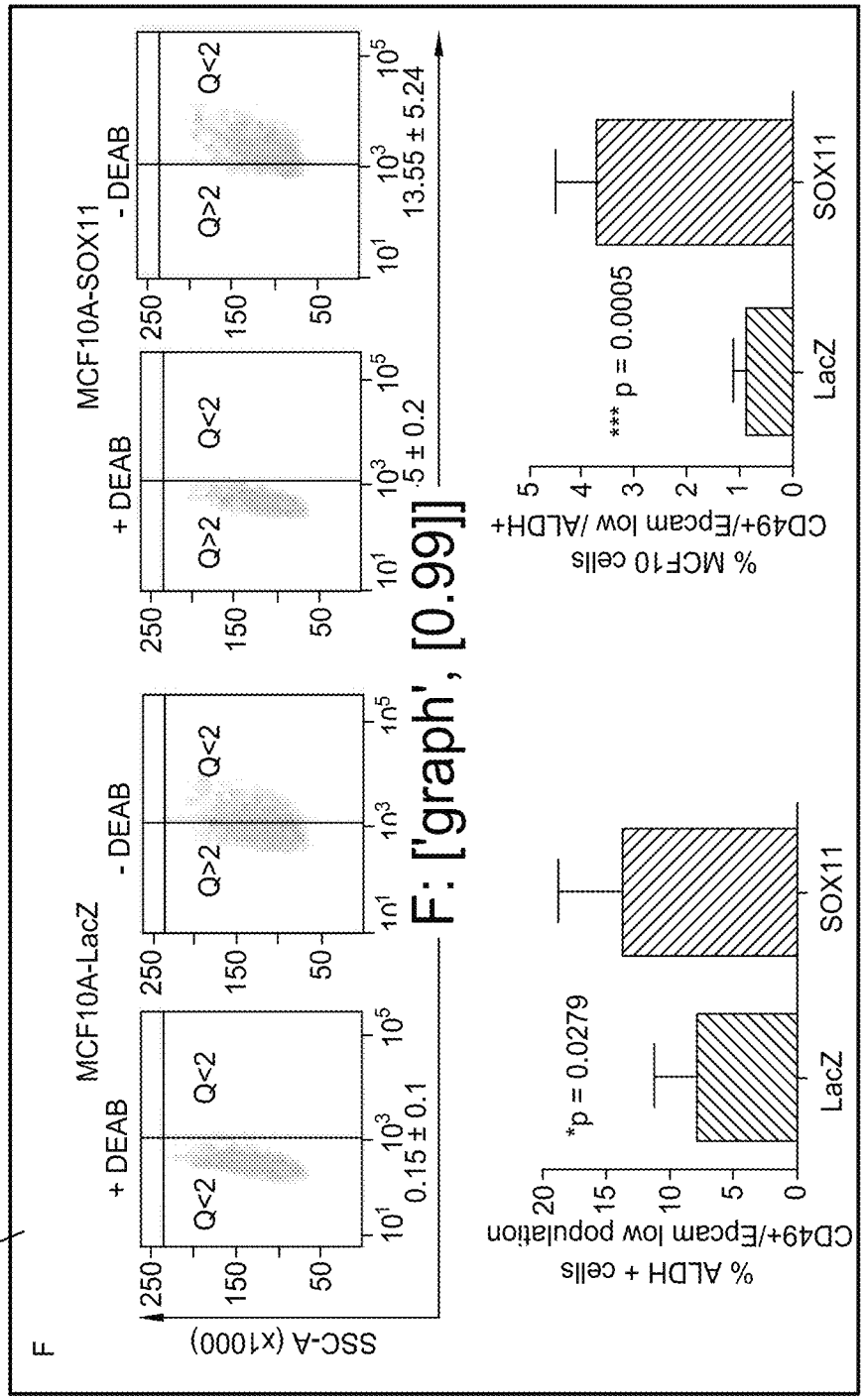
FIG. 4F2

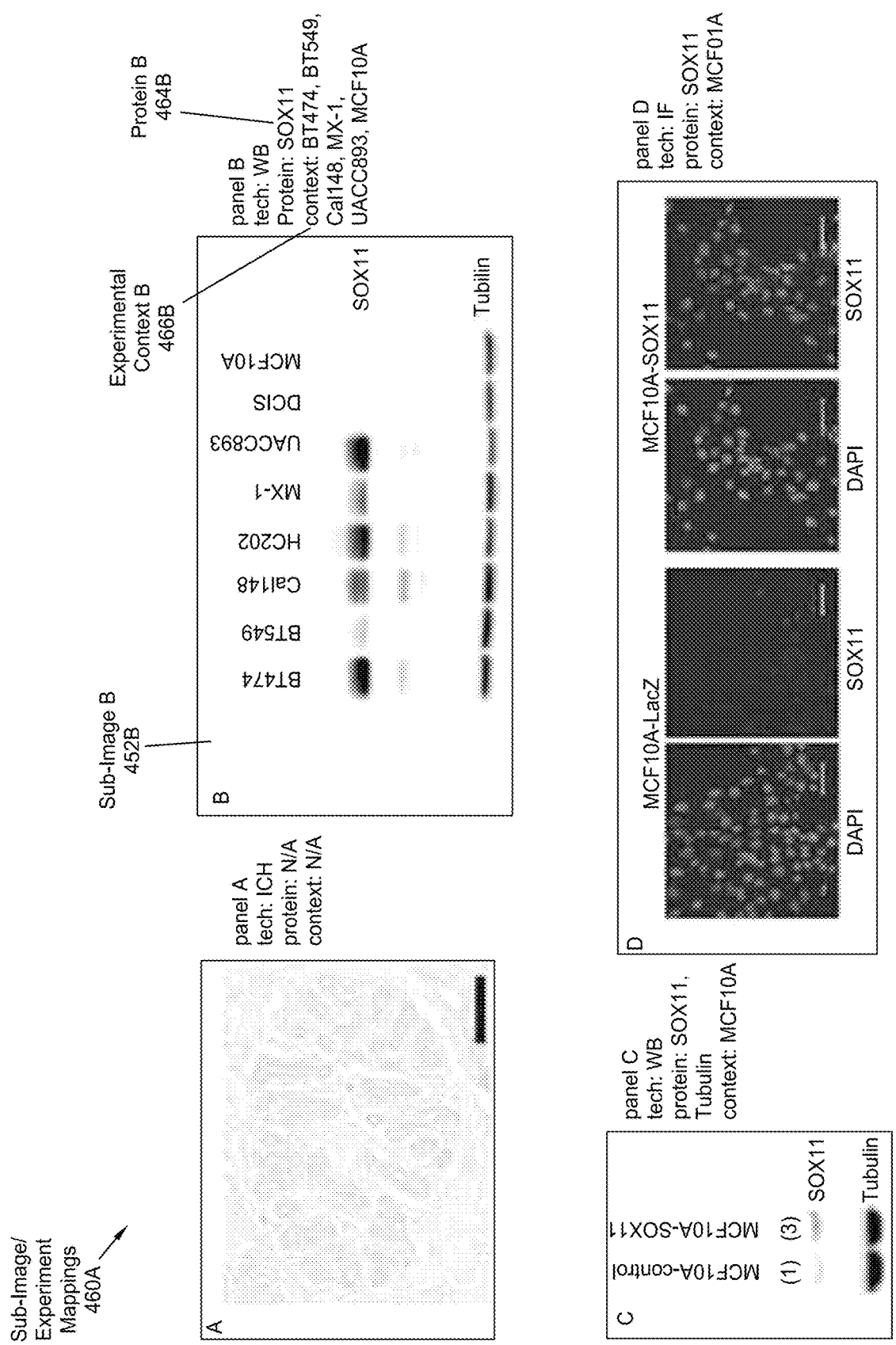
FIG. 4G1

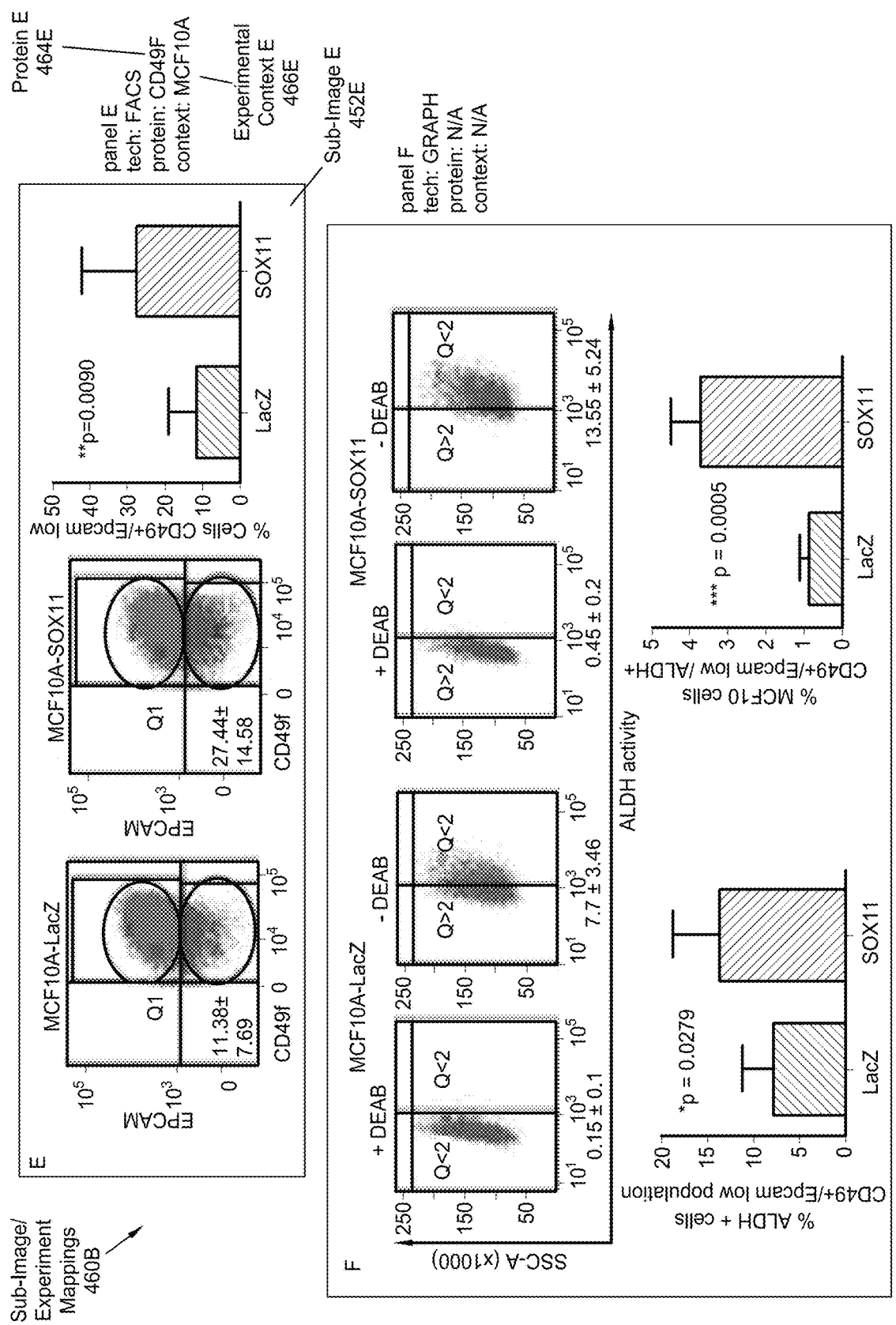
FIG. 4G2

DETERMINING EXPERIMENTS REPRESENTED BY IMAGES IN DOCUMENTS

BACKGROUND

Natural language processing (NLP) technology has often been used to analyze scientific documents. One common goal of such analysis is the identification of experiments described in the scientific document. However, there may be relevant information about the experiments that is not contained within the text of a scientific document. For example, images in the scientific document may include information regarding aspects of experiments not described in the body of text of the scientific document. The images may be complex, including heterogeneous elements, making it difficult to train machine learning models. In addition, an image may represent the results of multiple experiments in different sub-images, each of which needs to be understood as a distinct unit.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, one or more embodiments relate to a method including acquiring one or more image texts from an image of a document, segmenting the image into one or more sub-images using the one or more image texts, determining, by applying a machine learning model, one or more experimental techniques of one or more experiments for the one or more sub-images, and adding, to a knowledge base, one or more mappings of the one or more sub-images to the one or more experiments.

In general, in one aspect, one or more embodiments relate to a system including a memory coupled to a computer processor, a repository configured to store a document including an image including one or more image texts, a machine learning model, and a knowledge base. The system further includes an image analyzer transformer, executing on the computer processor and using the memory, configured to acquire the one or more image texts from the image, segment the image into one or more sub-images using the one or more image texts, determine, by applying the machine learning model, one or more experimental techniques of one or more experiments for the one or more sub-images, and add, to the knowledge base, one or more mappings of the one or more sub-images to the one or more experiments.

In general, in one aspect, one or more embodiments relate to a non-transitory computer readable medium including instructions that, when executed by a computer processor, perform: acquiring one or more image texts from an image of a document, segmenting the image into one or more sub-images using the one or more image texts, determining, by applying a machine learning model, one or more experimental techniques of one or more experiments for the one or more sub-images, and adding, to a knowledge base, one or more mappings of the one or more sub-images to the one or more experiments.

Other aspects of the invention will be apparent from the following description and the appended claims.

BRIEF DESCRIPTION OF DRAWINGS

FIGS. 4A1, 4A2, FIG. 4B, FIGS. 4C, 4D1, and 4D2 show examples in accordance with one or more embodiments of the invention.

FIGS. 4E1, 4E2, FIGS. 4F1, 4F2, FIGS. 4G1, 4G2, and FIG. 4H show examples in accordance with one or more embodiments of the invention.

DETAILED DESCRIPTION

Figure 1:
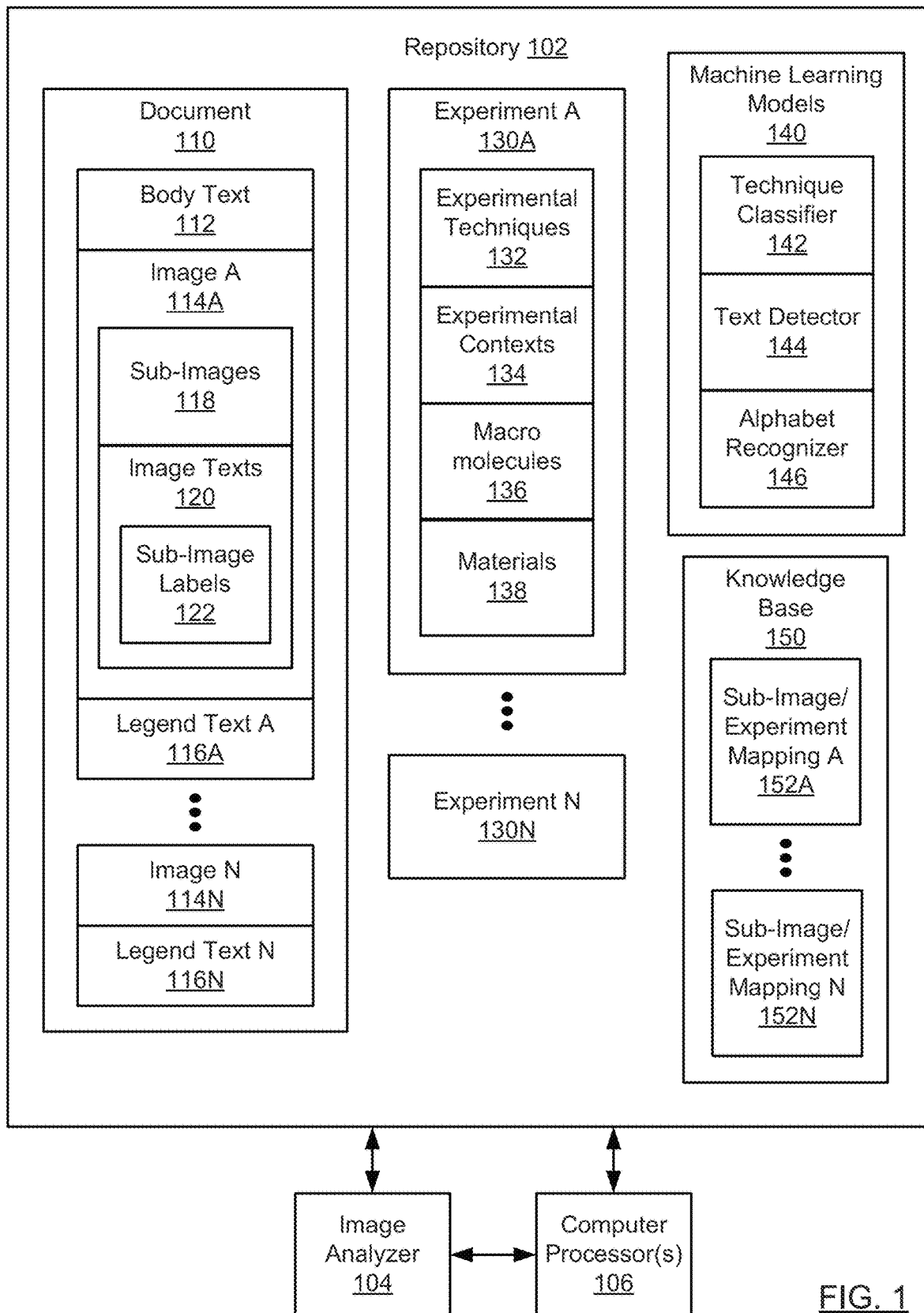
FIG. 1 shows a system in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In general, embodiments of the invention are directed to determining experiments represented by an image in a document. In one or more embodiments, image texts acquired from the image are used to segment the image into sub-images. For example, some of the image texts may be sub-image labels that are in close proximity to the sub-images. Legend text associated with the image may be divided into sub-legend texts corresponding to the sub-images. In one or more embodiments, the segmenting into sub-images is verified by matching the number of sub-legend texts to the number of sub-image labels. A trained machine learning model may classify the experimental techniques (e.g., immunohistochemistry (IHC), Western blotting (WB), etc.), corresponding to the experiments represented by the sub-images. Other attributes of the experiment, such as macromolecules (e.g., genes or proteins) and experimental contexts, may be determined by analyzing image texts in close proximity to the sub-images. The mappings of sub-images to experiments may be added to a knowledge base that supports querying and/or correlating various attributes of experiments.

FIG. 1 shows a computer system (100) in accordance with one or more embodiments of the invention. As shown in FIG. 1, the computer system (100) includes a repository (102), an image analyzer (104), and one or more computer processors (106). In one or more embodiments, the computer system (100) takes the form of the computing system (500) described with respect to FIG. 5A and the accompanying description below or takes the form of the client device (526) described with respect to FIG. 5B. In one or more embodiments, the computer processor(s) (106) takes the form of the computer processor(s) (502) described with respect to FIG. 5A and the accompanying description below.

In one or more embodiments, the repository (102) may be any type of storage unit and/or device (e.g., a file system, database, collection of tables, or any other storage mechanism) for storing data. Further, the repository (102) may include multiple different storage units and/or devices. The multiple different storage units and/or devices may or may not be of the same type or located at the same physical site.

In one or more embodiments, the repository (102) includes a document (110), experiments (130A, 130N), machine learning models (140), and a knowledge base (150). In one or more embodiments, the document (110) includes body text (112), images (114A, 114N) and legend texts (116A, 116N). For example, the document (110) may be an article in a scientific journal (e.g., a biochemistry or biomedical journal) describing experimental research. Alternatively, the document (110) may be a conference abstract, poster, research thesis, or patent. The body text (112) may include text of the document (110) that is external to the images (114A, 114N) and legend texts (116A, 116N).

In one or more embodiments, images (114A, 114N) are graphical representations that describe experiments (130A, 130N). For example, images (114A, 114N) may be represented as bitmaps (e.g., using the Joint Photographic Experts Group (JPEG) or Portable Network Graphic (PNG) format). Alternatively, images (114A, 114N) may be represented in the Portable Document Format (PDF) or some other format. In one or more embodiments, an image (114A) includes sub-images (118) and image texts (120). The sub-images (118) may be components of the image (114A) corresponding to separate experiments (130A, 130N). For example, each sub-image may describe the results of one or more experiments (130A, 130N). In one or more embodiments, the boundary of a sub-image (118) is defined by a region (e.g., a rectangle) surrounding the sub-image (118), referred to as a bounding box. The bounding box may indicate a location within the image (114A). For example, the location may be specified in terms of a coordinate system (e.g., Cartesian coordinates).

In one or more embodiments, image texts (120) include text that is within the image (114A). The boundary of an image text (120) may be defined by a bounding box surrounding the image text (120). An image text (120) may include features. For example, a color feature associated with the image text (120) may correspond to a specific experimental context (134) used in an experiment (130A).

An image text (120) may describe a sub-image (118). For example, image texts (120) may be labels of axes in a graph describing the results of an experiment (130A). In one or more embodiments, image texts (120) include sub-image labels (122). A sub-image label (122) may indicate a boundary of a sub-image (118). For example, an image (114A) may have 3 sub-images that are identified by sub-image labels "A", "B", and "C", where each sub-image label is in close proximity to the corresponding sub-image. In one or more embodiments, legend text (116A) includes text that describes the corresponding image (114A). For example, the legend text (116A) may summarize the experiments (130A, 130N) described in the image (114A).

In one or more embodiments, an experiment (130A) includes one or more experimental techniques (132), one or more experimental contexts (134), one or more macromolecules (136), and one or more materials (138). The experimental technique (132) may be a scientific technique used in the experiment (130A). Examples of experimental techniques (132) may include immunohistochemistry (IHC), Western blotting (WB), immunofluorescence (IF), Flow Cytometry (FC), fluorescence-activated cell sorting (FACS), etc. The experimental context (134) may include environmental conditions and/or contextual factors used in the experiment (130A). For example, the experimental context (134) may include cell line, temperature, duration, tissues used, materials used, disease model, etc.

In one or more embodiments, the macromolecule (136) includes molecules generated by polymerization of smaller subunits. For example, the subunits may be nucleic acids and/or peptides, such as genes and/or proteins. A protein may be a functional product of a gene. In one or more embodiments, the macromolecule (136) is a gene being studied in the experiment (130A). In one or more embodiments, the macromolecule (136) is a protein being studied in the experiment (130A). For example, the macromolecule (136) may be a protein being targeted by an antibody used in the experiment (130A). Multiple macromolecules (136) may be studied in the experiment (130A). A material (138) may be a substance that is used during the experiment (130A). For example, a material (138) may be consumed (e.g., reagent) or utilized (e.g., equipment).

In one or more embodiments, the machine learning models (140) includes a technique classifier (142), a text detector (144), and an alphabet recognizer (146). The machine learning models (140) may be various types of deep learning classifiers such as a neural network classifier (e.g., based on convolutional neural networks (CNNs)), random forest classifier, SGD classifier, lasso classifier, gradient boosting classifier, bagging classifier, ada boost classifier, ridge classifier, elastic net classifier, or NuSVR classifier. Deep learning, also known as deep structured learning or hierarchical learning, is part of a broader family of machine learning methods based on learning data representations, as opposed to task-specific algorithms. A machine learning model (140) may assign a confidence level to each classification performed by the machine learning model (140). The technique classifier (142) may be trained to classify an experimental technique (132) corresponding to a sub-image (118). For example, the technique classifier (142) may be a CNN that is trained using sub-images (118) labeled with an experimental technique (132). The sub-images (118) used in training may have bounding boxes that specify the boundary of the corresponding sub-image (118).

In one or more embodiments, the technique classifier (142) is trained to classify sub-images (118) into primary classes and filter classes. The primary classes may correspond to experimental techniques (132) (e.g., IHC, WB, IF, FACS, etc.) used in experiments (130A, 130N). In contrast, the filter classes may correspond to "false positives" that do not correspond to an experimental technique used in an experiment. For example, a sub-image initially classified under a primary class, may be re-classified as a false positive if the sub-image may also be classified under a filter class. In other words, a sub-image classified under a filter class may be considered to have no recognized experimental technique.

The text detector (144) may be trained to detect image texts (120) within an image (114A). For example, the text detector (144) may be a CNN that is trained using portions of images (114A, 114N) labeled as image texts (120). The alphabet recognizer (146) may be trained to detect sub-image labels (122) within an image (114A). For example, the alphabet recognizer (146) may be a CNN that is trained using image texts (120) labeled as sub-image labels (122). The alphabet recognizer (146) may be especially useful due to the ineffectiveness of traditional optical character recognition (OCR) technology in identifying single letters at the resolution typically encountered in sub-images (118).

In one or more embodiments, the knowledge base (150) includes sub-image/experiment mappings (152A, 152N). A sub-image/experiment mapping (152A) may be a mapping from a sub-image (118) to an experiment (130A). In other words, the sub-image/experiment mapping (152A) identifies the experiment (130A) represented by the corresponding sub-image (118).

In one or more embodiments, the image analyzer (104) may be implemented in hardware (e.g., circuitry), software, firmware, and/or any combination thereof. In one or more embodiments, the image analyzer (104) includes functionality to apply the text detector (144) to acquire image texts (120) from an image (114A). The image analyzer (104) may include functionality to segment an image (114A) into sub-images (118). The image analyzer (104) may include functionality to apply the technique classifier (142) to determine experimental techniques (132) of experiments (130A, 130N) represented by sub-images (118). The image analyzer (104) may include functionality to determine macromolecules (136), experimental contexts (134) and/or materials (138) of experiments (130A, 130N) represented by sub-images (118). The image analyzer (104) may include functionality to add sub-image/experiment mappings (152A, 152N) to a knowledge base (150).

In one or more embodiments, the computer processor (106) includes functionality to execute the image analyzer (104).

While FIG. 1 shows a configuration of components, other configurations may be used without departing from the scope of the invention. For example, various components may be combined to create a single component. As another example, the functionality performed by a single component may be performed by two or more components.

Figure 2:
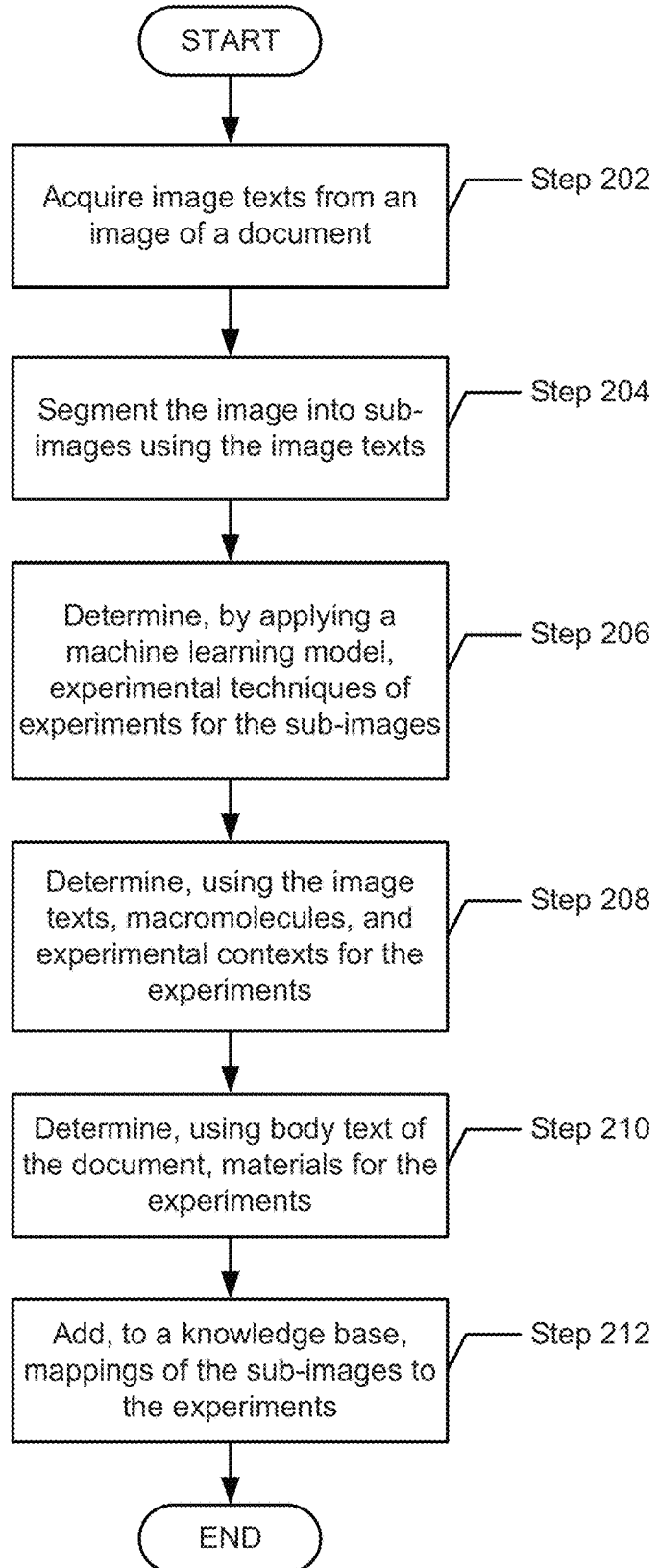
FIG. 2 and FIG. 3 show flowcharts in accordance with one or more embodiments of the invention.

FIG. 2 shows a flowchart in accordance with one or more embodiments of the invention. The flowchart depicts a process for determining experiments represented by an image. One or more of the steps in FIG. 2 may be performed by the components (e.g., the image analyzer (104) of the computer system (100)), discussed above in reference to FIG. 1. In one or more embodiments of the invention, one or more of the steps shown in FIG. 2 may be omitted, repeated, and/or performed in parallel, or in a different order than the order shown in FIG. 2. Accordingly, the scope of the invention should not be considered limited to the specific arrangement of steps shown in FIG. 2.

Initially, in Step 202, image texts are acquired from an image of a document. The image analyzer may preprocess (e.g., resize) the image before acquiring the image. In addition, the image analyzer may normalize, rotate and/or process the image texts using optical character recognition (OCR). In one or more embodiments, the image analyzer applies the text detector to acquire the image texts from the image. Alternatively, the image analyzer may use one or more image processing algorithms to acquire the image texts. For example, an image processing algorithm (e.g., the Maximally Stable Extremal Regions (MSER) algorithm) may identify, within the image, a candidate image text in a region whose dimensions satisfy a predetermined metric. Continuing this example, the predetermined metric may be used to filter out candidate image texts in very large or very small regions (e.g., to filter out false positives). The image analyzer may obtain, from the text detector, bounding boxes (e.g., regions) that encompass the image texts acquired by the text detector. Alternatively, the image analyzer may obtain, from an image processing algorithm, bounding boxes that encompass the image texts acquired by the image processing algorithm.

In Step 204, the image is segmented into sub-images using the image texts. The image analyzer may segment the image into sub-images by determining bounding boxes for the sub-images. See description of FIG. 3 below for an explanation of how sub-image labels may be used to segment the image into sub-images.

In Step 206, experimental techniques of experiments for the sub-images are determined by applying a machine learning model. The image analyzer may apply the technique classifier to the sub-images to determine the experimental techniques. In one or more embodiments, the technique classifier determines that a sub-image has no recognized experimental technique when the technique classifier classifies the sub-image as a filter class.

In Step 208, macromolecules and experimental contexts are determined for the experiments using the image texts. In one or more embodiments, the image analyzer may use an optical character recognition (OCR) algorithm and/or a natural language processing (NLP) capability to identify keywords in the image texts that are associated with macromolecules and/or experimental contexts. For example, the image analyzer may match a keyword acquired from the image texts against a list of known macromolecule names. Similarly, the image analyzer may match a keyword acquired from the image texts against a list of known experimental contexts. In one or more embodiments, the determination of macromolecules and experimental contexts is further based on analyzing sub-legend texts associated with sub-image labels in Step 306 below. For example, the image analyzer may match a keyword acquired from the sub-legend text corresponding to a sub-image against a list of known macromolecule names.

In one or more embodiments, in order to assess the relevance of keywords included in an image text to an experiment corresponding to a sub-image, the image analyzer analyzes the locations of the image text and the sub-image. For example, the keywords may be considered relevant when the bounding box for the sub-image overlaps or encloses the bounding box for the image text. Alternatively, the image analyzer may determine a distance between the image text and the sub-image based on the relative locations of the bounding boxes for the image text and the sub-image. For example, the keywords may be considered relevant when the distance between the bounding boxes for the image text and the sub-image falls within a threshold distance. Additional factors affecting the relevance of keywords may include: the angles between the bounding boxes for the image text and the sub-image, the sizes of the image text and the sub-image, etc. In one or more embodiments, the image analyzer determines an experimental context for a sub-image based on a color feature associated with the relevant image text.

In one or more embodiments, the image analyzer determines a relationship between experiments corresponding to sub-images. For example, experiments whose attributes overlap (e.g., experiments with the same experimental technique and/or macromolecule) may comprise a sequence of experiments.

In Step 210, materials are determined for the experiments using body text of the document. In one or more embodiments, the image analyzer identifies keywords in the body text (e.g., in a "materials and methods" section of the document) that are associated with materials (e.g., reagents and/or equipment). For example, the image analyzer may match a keyword acquired from the body text against a list of known material names. Materials may be unlikely to be described in image texts since materials may be used during the experiment without contributing directly to the results of the experiment.

In Step 212, mappings of the sub-images to the experiments are added to a knowledge base. The knowledge base may be queried to search for and/or correlate various attributes of experiments (e.g., experimental techniques, experimental contexts, macromolecules, and materials) corresponding to sub-images. In one or more embodiments, the knowledge base additionally includes mappings of the sub-images to each of the parameters of the experiment (e.g., experimental techniques, experimental contexts, macromolecules, and/or materials).

Figure 3:
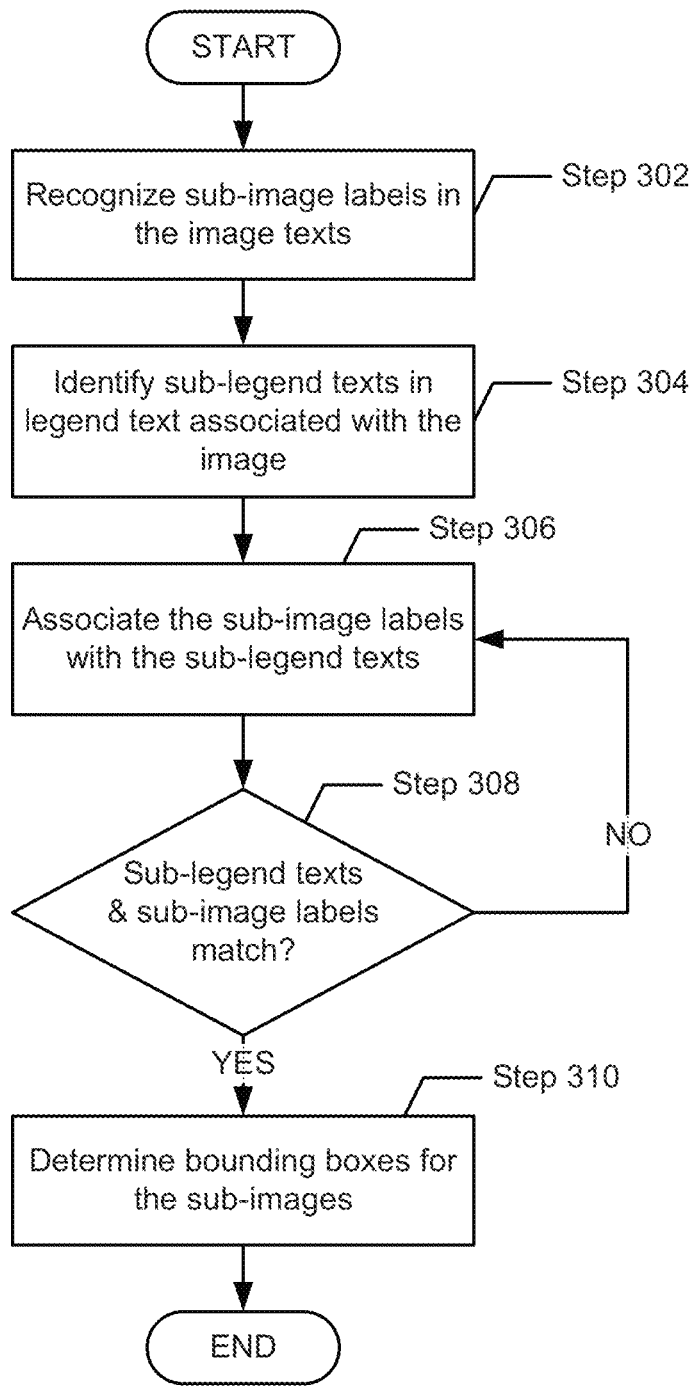

FIG. 3 shows a flowchart in accordance with one or more embodiments of the invention. The flowchart depicts a process for segmenting an image. Moreover, the flowchart in FIG. 3 may correspond to Step 204 in FIG. 2. One or more of the steps in FIG. 3 may be performed by the components (e.g., the image analyzer (104) of the computer system (100)), discussed above in reference to FIG. 1. In one or more embodiments of the invention, one or more of the steps shown in FIG. 3 may be omitted, repeated, and/or performed in parallel, or in a different order than the order shown in FIG. 3. Accordingly, the scope of the invention should not be considered limited to the specific arrangement of steps shown in FIG. 3.

Initially, in Step 302, sub-image labels are recognized in the image texts (also see description of Step 202 above). In one or more embodiments, the image analyzer applies the alphabet recognizer to the image texts to recognize the sub-image labels. In one or more embodiments, the alphabet recognizer determines which image texts are sub-image labels using features including: aspect ratio, size, and/or relative positions and angles between sub-image labels. In order to compensate for variations in label placement and image resolution, the alphabet recognizer may preprocess the image by shifting the color space to red-green-blue (RGB) and/or increasing the image size.

In Step 304, sub-legend texts in legend text associated with the image are identified. The image analyzer may identify the sub-legend texts by parsing the legend text. For example, the image analyzer may parse the legend text into a parse tree or sentence map. Continuing this example, the sub-legend text may include one or more sentences describing the experiment represented by the sub-image. In one or more embodiments, the image analyzer uses the number of sub-legend texts as an upper bound on the number of sub-images resulting from segmenting the image, as described in Step 310 below.

In Step 306, the sub-image labels are associated with the sub-legend texts. For example, the association may be based on scoring the sub-image labels regarding a likelihood of a match between the sub-legend text and the sub-image label (e.g., the likelihood that both the sub-legend text and the sub-image label indicate the same letter or number).

If, in Step 308 a determination is made that the sub-legend texts and the sub-image labels match, then Step 310 below is performed. In one or more embodiments, the sub-legend texts and the sub-image labels match when the number of sub-legend texts equals the number of sub-image labels. In one or more embodiments, the sub-legend texts and the sub-image labels match when the contents of the sub-legend texts match the contents of the sub-image labels. For example, a sub-legend text that includes the capital letter "B" may match the sub-image label "B".

Otherwise, if in Step 308 a determination is made that the sub-legend texts and the sub-image labels fail to match, then Step 306 above is again executed, to make another attempt at associating the sub-image labels with the sub-legend texts. In one or more embodiments, when the sub-legend texts and the sub-image labels fail to match, the image analyzer determines whether to use the sub-image labels or the sub-legend texts for the next attempt at associating the sub-image labels with the sub-legend texts. In other words, when there is a mismatch, the image analyzer determines which is more reliable: the sub-image labels or the sub-legend texts. For example, the image analyzer may determine whether to use the sub-image labels or the sub-legend texts based on the confidence levels associated with sub-legend texts and the sub-image labels (e.g., the confidence levels assigned by the alphabet recognizer).

In Step 310, bounding boxes for the sub-images are determined. In one or more embodiments, the bounding box for a sub-image includes the bounding box for a sub-image label. The sub-image label may be a closest sub-image label to the sub-image, based on a distance measure. For example, a distance between the sub-image label and the sub-image may be based on the relative locations of the bounding boxes for the sub-image label and the sub-image. In one or more embodiments, the bounding boxes for the sub-images are selected to minimize an image segmenting metric that aggregates the distances between sub-images and corresponding sub-image labels.

Figure 4H:
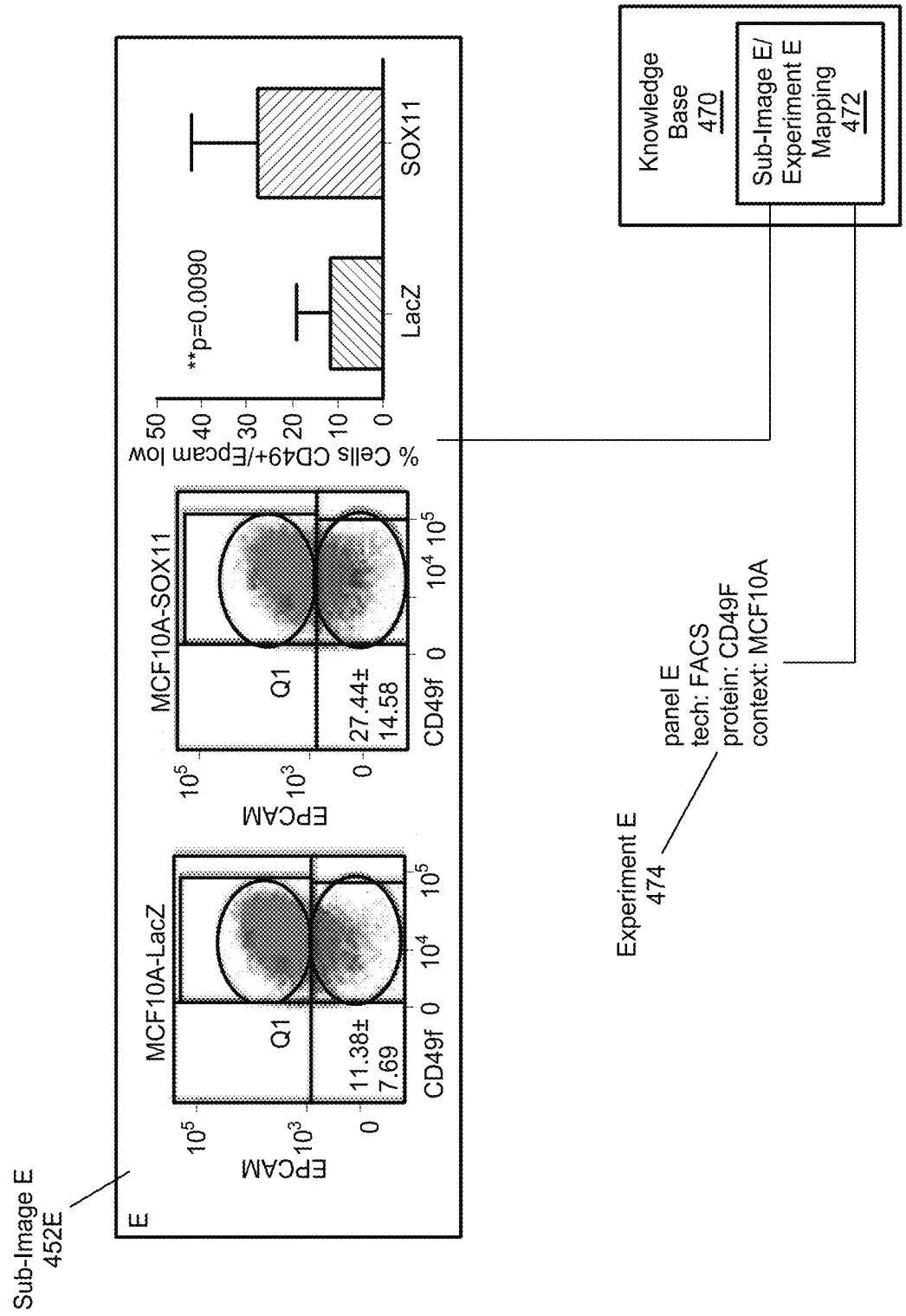

The following example is for explanatory purposes only and not intended to limit the scope of the invention. FIGS. 4A1, 4A2, FIG. 4B, FIG. 4C, FIGS. 4D1, 4D2, FIGS. 4E1, 4E2, FIGS. 4F1, 4F2, FIGS. 4G1, 4G2, and FIG. 4H show an implementation example in accordance with one or more embodiments of the invention. FIGS. 4A1 and 4A2 show images (400A and 400B) ((114A, 114N) in FIG. 1) of a document ((110) in FIG. 1). FIG. 4B shows legend text (410) ((116A, 116N) in FIG. 1) corresponding to the images (400A and 400B). As shown in FIG. 4C, the image analyzer ((104) in FIG. 1) identifies sub-legend texts (422A, 422B, 422C, 422D, 422E, 422F) by parsing the legend text (410) into sentences. As shown in FIGS. 4D1 and 4D2, the image analyzer next applies the text detector to acquire image texts (432A, 432B, 432C, 432D, 432E, 432F, 432Q, 432R, 432S, 432T, etc.) ((120) in FIG. 1) from the images (400A and 400B). The text detector provides a bounding box for each of the image texts (432A, 432B, 432C, 432D, 432E, 432F, 432Q, 432R, 432S, 432T, etc.). As shown in FIGS. 4E1 and 4E2, the image analyzer then applies the alphabet recognizer to recognize some of the image texts (i.e., 432A, 432B, 432C, 432D, 432E, 432F) as sub-image labels (442A, 442B, 442C, 442D, 442E, 442F) ((122) in FIG. 1).

As shown in FIGS. 4F1 and 4F2, the image analyzer next applies the technique classifier to determine the experimental techniques (e.g., 454A, 454B) ((132) in FIG. 1) of sub-images (452A, 452B, 452C, 452D, 452E, 452F) ((118) in FIG. 1). The image analyzer segments the images (400A and 400B) into the sub-images (452A, 452B, 452C, 452D, 452E, 452F) by first matching the sub-legend texts (422A, 422B, 422C, 422D, 422E, 422F) of FIG. 4C with the sub-image labels (442A, 442B, 442C, 442D, 442E, 442F) of FIGS. 4E1 and 4E2. The image analyzer then determines bounding boxes for each of the sub-images (452A, 452B, 452C, 452D, 452E, 452F) that include the bounding boxes for the sub-image labels (442A, 442B, 442C, 442D, 442E, 442F) closest to the bounding boxes for the sub-image (452A, 452B, 452C, 452D, 452E, 452F).

As shown in FIGS. 4G1 and 4G2, the image analyzer generates sub-image/experiment mappings (460A and 460B) by identifying keywords in the image texts associated with the corresponding sub-images. FIGS. 4G1 and 4G2 show that keywords in image texts whose bounding boxes are within the bounding box for sub-image B (452B) are used to determine the macromolecule, in this case, protein (464B) and experimental context (466B) for the experiment associated with sub-image B (452B). Similarly, FIGS. 4G1 and 4G2 show that keywords in image texts whose bounding boxes are within the bounding box for sub-image E (452E) are used to determine the protein (464E) and experimental context (466E) for the experiment associated with sub-image E (452E).

Finally, the image analyzer adds the sub-image/experiment mappings (460A and 460B) to a knowledge base. FIG. 4H illustrates a knowledge base (470) that includes the sub-image E/experiment E mapping (472), which maps sub-image E (452E) to experiment E (474).

Figure 5A:
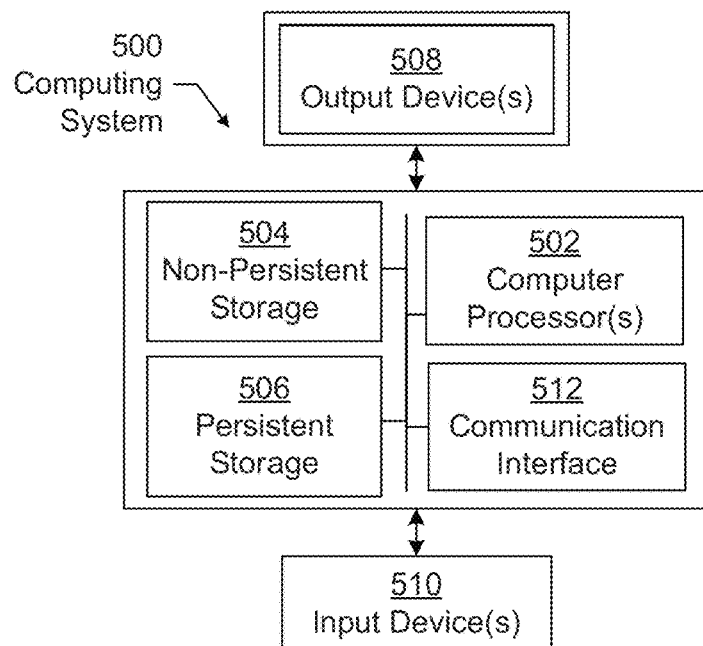
FIG. 5A and FIG. 5B show computing systems in accordance with one or more embodiments of the invention.

Embodiments disclosed herein may be implemented on a computing system. Any combination of mobile, desktop, server, router, switch, embedded device, or other types of hardware may be used. For example, as shown in FIG. 5A, the computing system (500) may include one or more computer processors (502), non-persistent storage (504) (e.g., volatile memory, such as random access memory (RAM), cache memory), persistent storage (506) (e.g., a hard disk, an optical drive such as a compact disk (CD) drive or digital versatile disk (DVD) drive, a flash memory, etc.), a communication interface (512) (e.g., Bluetooth interface, infrared interface, network interface, optical interface, etc.), and numerous other elements and functionalities.

The computer processor(s) (502) may be an integrated circuit for processing instructions. For example, the computer processor(s) (502) may be one or more cores or micro-cores of a processor. The computing system (500) may also include one or more input devices (510), such as a touchscreen, keyboard, mouse, microphone, touchpad, electronic pen, or any other type of input device.

The communication interface (512) may include an integrated circuit for connecting the computing system (500) to a network (not shown) (e.g., a local area network (LAN), a wide area network (WAN) such as the Internet, mobile network, or any other type of network) and/or to another device, such as another computing device.

Further, the computing system (500) may include one or more output devices (508), such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (502), non-persistent storage (504), and persistent storage (506). Many different types of computing systems exist, and the aforementioned input and output device(s) may take other forms.

Software instructions in the form of computer readable program code to perform embodiments disclosed herein may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments disclosed herein.

Figure 5B:
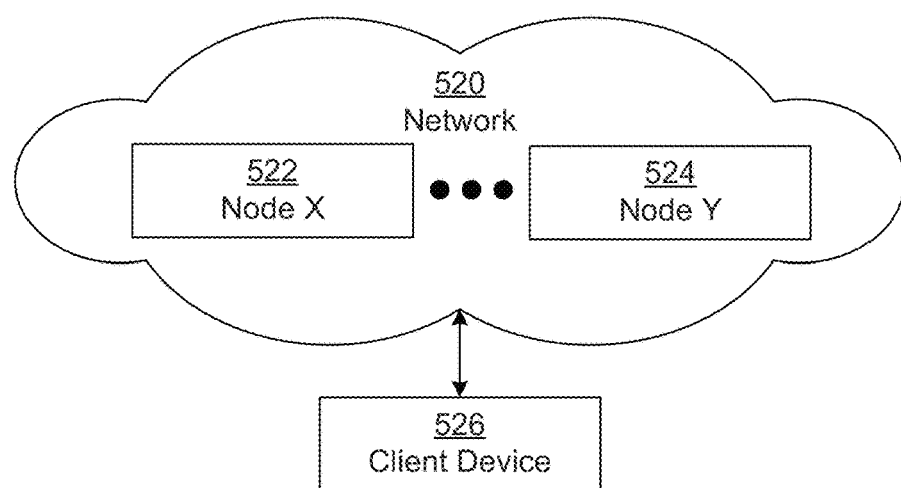

The computing system (500) in FIG. 5A may be connected to or be a part of a network. For example, as shown in FIG. 5B, the network (520) may include multiple nodes (e.g., node X (522), node Y (524)). Each node may correspond to a computing system, such as the computing system shown in FIG. 5A, or a group of nodes combined may correspond to the computing system shown in FIG. 5A. By way of an example, embodiments disclosed herein may be implemented on a node of a distributed system that is connected to other nodes. By way of another example, embodiments disclosed herein may be implemented on a distributed computing system having multiple nodes, where each portion disclosed herein may be located on a different node within the distributed computing system. Further, one or more elements of the aforementioned computing system (500) may be located at a remote location and connected to the other elements over a network.

Although not shown in FIG. 5B, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (e.g., node X (522), node Y (524)) in the network (520) may be configured to provide services for a client device (526). For example, the nodes may be part of a cloud computing system. The nodes may include functionality to receive requests from the client device (526) and transmit responses to the client device (526). The client device (526) may be a computing system, such as the computing system shown in FIG. 5A. Further, the client device (526) may include and/or perform all or a portion of one or more embodiments disclosed herein.

The computing system or group of computing systems described in FIGS. 5A and 5B may include functionality to perform a variety of operations disclosed herein. For example, the computing system(s) may perform communication between processes on the same or different system. A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided below.

Based on the client-server networking model, sockets may serve as interfaces or communication channel endpoints enabling bidirectional data transfer between processes on the same device. Foremost, following the client-server networking model, a server process (e.g., a process that provides data) may create a first socket object. Next, the server process binds the first socket object, thereby associating the first socket object with a unique name and/or address. After creating and binding the first socket object, the server process then waits and listens for incoming connection requests from one or more client processes (e.g., processes that seek data). At this point, when a client process wishes to obtain data from a server process, the client process starts by creating a second socket object. The client process then proceeds to generate a connection request that includes at least the second socket object and the unique name and/or address associated with the first socket object. The client process then transmits the connection request to the server process. Depending on availability, the server process may accept the connection request, establishing a communication channel with the client process, or the server process, busy in handling other operations, may queue the connection request in a buffer until server process is ready. An established connection informs the client process that communications may commence. In response, the client process may generate a data request specifying the data that the client process wishes to obtain. The data request is subsequently transmitted to the server process. Upon receiving the data request, the server process analyzes the request and gathers the requested data. Finally, the server process then generates a reply including at least the requested data and transmits the reply to the client process. The data may be transferred, more commonly, as datagrams or a stream of characters (e.g., bytes).

Shared memory refers to the allocation of virtual memory space in order to substantiate a mechanism for which data may be communicated and/or accessed by multiple processes. In implementing shared memory, an initializing process first creates a shareable segment in persistent or non-persistent storage. Post creation, the initializing process then mounts the shareable segment, subsequently mapping the shareable segment into the address space associated with the initializing process. Following the mounting, the initializing process proceeds to identify and grant access permission to one or more authorized processes that may also write and read data to and from the shareable segment. Changes made to the data in the shareable segment by one process may immediately affect other processes, which are also linked to the shareable segment. Further, when one of the authorized processes accesses the shareable segment, the shareable segment maps to the address space of that authorized process. Often, only one authorized process may mount the shareable segment, other than the initializing process, at any given time.

Other techniques may be used to share data, such as the various data described in the present application, between processes without departing from the scope of the invention. The processes may be part of the same or different application and may execute on the same or different computing system.

The computing system in FIG. 5A may implement and/or be connected to a data repository. For example, one type of data repository is a database. A database is a collection of information configured for ease of data retrieval, modification, re-organization, and deletion. Database Management System (DBMS) is a software application that provides an interface for users to define, create, query, update, or administer databases.

The user, or software application, may submit a statement or query into the DBMS. Then the DBMS interprets the statement. The statement may be a select statement to request information, update statement, create statement, delete statement, etc. Moreover, the statement may include parameters that specify data, or data container (database, table, record, column, view, etc.), identifier(s), conditions (comparison operators), functions (e.g. join, full join, count, average, etc.), sort (e.g. ascending, descending), or others. The DBMS may execute the statement. For example, the DBMS may access a memory buffer, a reference or index a file for read, write, deletion, or any combination thereof, for responding to the statement. The DBMS may load the data from persistent or non-persistent storage and perform computations to respond to the query. The DBMS may return the result(s) to the user or software application.

The above description of functions presents only a few examples of functions performed by the computing system of FIG. 5A and the nodes and/or client device in FIG. 5B. Other functions may be performed using one or more embodiments disclosed herein.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method, comprising:
   acquiring, from a document, (i) one or more image texts of an image and (ii) a plurality of sub-legend texts, wherein the image is a visual representation of one or more experiments;
   segmenting the image into one or more sub-images by:
      recognizing a plurality of sub-image labels in the one or more image texts, wherein the plurality of sub-legend texts describe one or more experiments corresponding to the one or more sub-images, and
      for each sub-legend text of the plurality of sub-legend texts, attempting a match between the sub-legend text and a sub-image label of the plurality of sub-image labels by:
         determining whether the number of sub-legend texts equals the number of sub-image labels, and
         determining whether the sub-legend text comprises the sub-image label;
   for each sub-image of the one or more sub-images, determining, by applying a machine learning model, that the sub-image is a visual representation of an experimental technique used in the one or more experiments; and
   adding, to a knowledge base, one or more mappings of the one or more sub-images to the one or more experiments.

2. The method of claim 1, further comprising:
   determining, using body text of the document, materials for the one or more experiments.

3. The method of claim 1, further comprising:
   classifying, by the machine learning model, a sub-image of the one or more sub-images as a filter class; and
   in response to classifying the sub-image as the filter class, determining that the sub-image has no recognized experimental technique.

4. The method of claim 1, further comprising:
   determining one or more bounding boxes within the image for the one or more sub-images.

5. The method of claim 4, further comprising:
   obtaining one or more bounding boxes within the image for the one or more image texts, wherein the match is attempted using the one or more bounding boxes for the one or more sub-images and the one or more bounding boxes for the one or more sub-image labels.

6. The method of claim 5, further comprising:
determining macromolecules and experimental contexts for the one or more experiments using the one or more image texts, the one or more bounding boxes for the one or more sub-images, and the one or more bounding boxes for the one or more image texts.

7. A system, comprising:
a memory coupled to a computer processor;
a repository configured to store:
 a document comprising (i) an image comprising one or more image texts and (ii) a plurality of sub-legend texts, wherein the image is a visual representation of one or more experiments,
 a machine learning model, and
 a knowledge base; and
an image analyzer, executing on the computer processor and using the memory, configured to:
 acquire, from the document, (i) the one or more image texts of the image and (ii) the plurality of sub-legend texts,
 segment the image into one or more sub-images by:
  recognizing a plurality of sub-image labels in the one or more image texts, wherein the plurality of sub-legend texts describe one or more experiments corresponding to the one or more sub-images, and
  for each sub-legend text of the plurality of sub-legend texts, attempting a match between the sub-legend text and a sub-image label of the plurality of sub-image labels by:
   determining whether the number of sub-legend texts equals the number of sub-image labels, and
   determining whether the sub-legend text comprises the sub-image label,
 for each sub-image of the one or more sub-images, determine, by applying the machine learning model, that the sub-image is a visual representation of an experimental technique used in the one or more experiments, and
 add, to the knowledge base, one or more mappings of the one or more sub-images to the one or more experiments.

8. The system of claim 7, wherein the image analyzer is further configured to:
determine, using body text of the document, materials for the one or more experiments.

9. The system of claim 7, wherein the image analyzer is further configured to:
classify, by the machine learning model, a sub-image of the one or more sub-images as a filter class; and
in response to classifying the sub-image as the filter class, determine that the sub-image has no recognized experimental technique.

10. The system of claim 7, wherein the image analyzer is further configured to:
determine one or more bounding boxes within the image for the one or more sub-images.

11. The system of claim 10, wherein the image analyzer is further configured to:
obtain one or more bounding boxes within the image for the one or more image texts, wherein the match is attempted using the one or more bounding boxes for the one or more sub-images and the one or more bounding boxes for the one or more sub-image labels.

12. The system of claim 11, wherein the image analyzer is further configured to:
determine macromolecules and experimental contexts for the one or more experiments using the one or more image texts, the one or more bounding boxes for the one or more sub-images, and the one or more bounding boxes for the one or more image texts.

13. A non-transitory computer readable medium comprising instructions that, when executed by a computer processor, perform:
acquiring, from a document, (i) one or more image texts of an image and (ii) a plurality of sub-legend texts, wherein the image is a visual representation of one or more experiments;
segmenting the image into one or more sub-images by:
 recognizing a plurality of sub-image labels in the one or more image texts, wherein the plurality of sub-legend texts describe one or more experiments corresponding to the one or more sub-images, and
 for each sub-legend text of the plurality of sub-legend texts, attempting a match between the sub-legend text and a sub-image label of the plurality of sub-image labels by:
  determining whether the number of sub-legend texts equals the number of sub-image labels, and
  determining whether the sub-legend text comprises the sub-image label;
for each sub-image of the one or more sub-images, determining, by applying a machine learning model, that the sub-image is a visual representation of an experimental technique used in the one or more experiments; and
adding, to a knowledge base, one or more mappings of the one or more sub-images to the one or more experiments.

14. The non-transitory computer readable medium of claim 13, wherein the instructions further perform:
classifying, by the machine learning model, a sub-image of the one or more sub-images as a filter class; and
in response to classifying the sub-image as the filter class, determining that the sub-image has no recognized experimental technique.

15. The non-transitory computer readable medium of claim 13, wherein the instructions further perform:
determining one or more bounding boxes within the image for the one or more sub-images.

16. The non-transitory computer readable medium of claim 15, wherein the instructions further perform:
obtaining one or more bounding boxes within the image for the one or more image texts, wherein the match is attempted using the one or more bounding boxes for the one or more sub-images and the one or more bounding boxes for the one or more sub-image labels.

17. The non-transitory computer readable medium of claim 16, wherein the instructions further perform:
determining macromolecules and experimental contexts for the one or more experiments using the one or more image texts, the one or more bounding boxes for the one or more sub-images, and the one or more bounding boxes for the one or more image texts.

* * * * *